United States Patent
Morris et al.

(10) Patent No.: US 9,514,924 B2
(45) Date of Patent: *Dec. 6, 2016

(54) DROPLET MANIPULATION USING GAS-PHASE STANDING-WAVE ULTRASOUND FIELDS IN MS SOURCES

(71) Applicant: Micromass UK Limited, Wilmslow (GB)

(72) Inventors: Michael Raymond Morris, Glossop (GB); Steven Derek Pringle, Darwen (GB); Keith Richardson, High Peak (GB)

(73) Assignee: MICROMASS UK LIMITED, Wilmslow (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/719,665

(22) Filed: May 22, 2015

(65) Prior Publication Data

US 2015/0325421 A1 Nov. 12, 2015

Related U.S. Application Data

(63) Continuation of application No. 14/359,811, filed as application No. PCT/GB2012/052900 on Nov. 22, 2012, now Pat. No. 9,040,906.

(30) Foreign Application Priority Data

Nov. 22, 2011 (GB) .................................. 1120143.1

(51) Int. Cl.
| | |
|---|---|
| *H01J 49/26* | (2006.01) |
| *H01J 49/16* | (2006.01) |
| *H01J 49/00* | (2006.01) |
| *H01J 49/02* | (2006.01) |
| *H01J 49/04* | (2006.01) |

(Continued)

(52) U.S. Cl.
CPC .......... *H01J 49/165* (2013.01); *G01N 27/622* (2013.01); *G01N 29/22* (2013.01); *H01J 49/0031* (2013.01); *H01J 49/022* (2013.01); *H01J 49/0454* (2013.01); *H01J 49/24* (2013.01);

(Continued)

(58) Field of Classification Search
USPC ................................ 250/281, 282, 283, 288
See application file for complete search history.

(56) References Cited

U.S. PATENT DOCUMENTS

| | | | |
|---|---|---|---|
| 4,863,491 | A | 9/1989 | Brandt et al. |
| 6,126,086 | A | 10/2000 | Browner et al. |

(Continued)

FOREIGN PATENT DOCUMENTS

JP     2012054172     3/2012

OTHER PUBLICATIONS

Enke, "A Predictive Model for Matrix and Analyte Effects in Electrospray Ionization of Singly-Charged Ionic Analytes", Analytical Chemistry, vol. 69, No. 23, pp. 4885-4893, 1997.

*Primary Examiner* — Nicole Ippolito
(74) *Attorney, Agent, or Firm* — Diederiks & Whitelaw, PLC

(57) ABSTRACT

An ion source for a mass spectrometer is disclosed comprising an ionization device which emits a stream of droplets and one or more ultrasonic transmitters which create one or more acoustic standing waves. The acoustic standing waves may be used to further nebulize the stream of droplets and induce internal mixing of the droplets.

23 Claims, 1 Drawing Sheet

(51) Int. Cl.
*G01N 27/62* (2006.01)
*G01N 29/22* (2006.01)
*H01J 49/24* (2006.01)

(52) U.S. Cl.
CPC ......... *H01J 49/26* (2013.01); *Y10T 137/0391* (2015.04); *Y10T 137/206* (2015.04)

(56) References Cited

U.S. PATENT DOCUMENTS

| | | |
|---|---|---|
| 6,586,731 B1 | 7/2003 | Joliffe |
| 6,909,091 B2 | 6/2005 | Nilsson et al. |
| 7,208,727 B2 | 4/2007 | Fedorov et al. |
| 7,260,483 B2 | 8/2007 | Gard et al. |
| 7,812,309 B2 | 10/2010 | Guevremont et al. |
| 8,680,460 B2 | 3/2014 | Loucks et al. |
| 9,040,906 B2* | 5/2015 | Morris et al. ................. 250/288 |
| 2006/0289747 A1* | 12/2006 | Schultz ................ G01N 27/622 250/294 |

* cited by examiner

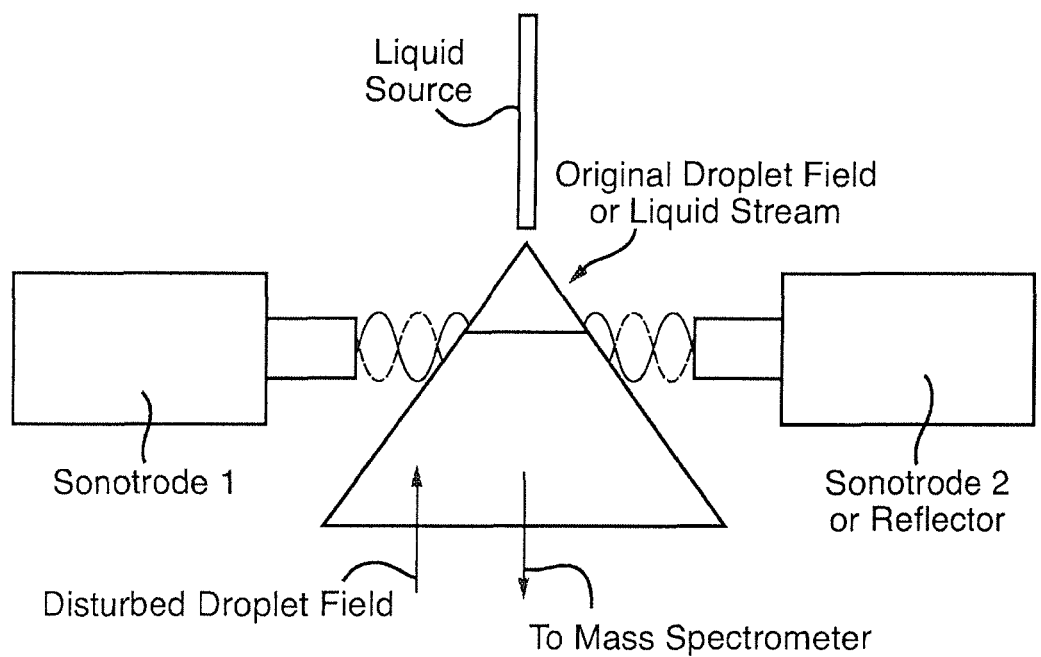

ant application Ser. No. 14/359,811 filed 21 May 2014
DROPLET MANIPULATION USING GAS-PHASE STANDING-WAVE ULTRASOUND FIELDS IN MS SOURCES

CROSS-REFERENCE TO RELATED APPLICATIONS

This application is the continuation application U.S. patent application Ser. No. 14/359,811 filed 21 May 2014 which is the National Stage of International Application No. PCT/GB2012/052900, filed 22 Nov. 2012, which claims priority from and the benefit of United Kingdom Patent Application No. 1120143.1 filed on 22 Nov. 2011. The entire content of this application is incorporated herein by reference.

BACKGROUND OF THE PRESENT INVENTION

It is known that gas-phase acoustic fields induce local pressure differences around the surfaces of liquid droplets (King, L. V. Proc. Roy. Soc., A147, 212-240 (1934)). The forces produced by acoustic standing waves are significantly larger than those produced by travelling waves. Acoustic standing waves can be produced either using an ultrasound transmitter (sonotrode) and a reflector or by using a pair of ultrasound transmitters.

It is known to cause droplets to be levitated in the nodes of standing-wave ultrasound fields. Similar techniques are used for lateral stabilization of droplet position in wind tunnels in which droplets are suspended vertically by balancing gravitational and aerodynamic forces (Lupi, V. D., Hansman, L. J. Journal of Atmospheric and Oceanic Technology, 8, 541-552, (1991)). Under appropriate conditions, droplet breakup can also be induced, and this effect can be used to atomize streams of liquid.

It is also known, for example, to use an ultrasonic standing wave arrangement to produce a paint spray mist for painting a workpiece.

It is desired to provide an improved ion source and method of ionising a sample.

SUMMARY OF THE PRESENT INVENTION

According to an aspect of the present invention there is provided an ion source for a mass spectrometer comprising:

an ionisation device arranged and adapted to emit a stream of droplets; and one or more ultrasonic transmitters or sonotrodes arranged and adapted to create one or more acoustic standing waves downstream of the ionisation device.

One of the problems with certain types of conventional ion sources such as Electrospray ion sources is that they can emit droplets at least some of which have a relatively large diameter. The relatively large droplets do not then completely desolvate which results in a loss of analyte signal. The solution to this problem according to the present invention is to provide one or more ultrasonic transmitters downstream of the ionisation device (e.g. Electrospray ion source). The one or more ultrasonic transmitters create acoustic standing waves which, for example, further nebulise the stream of droplets emitted from the ionisation device. As a result, the droplets are significantly reduced in size by the acoustic standing waves resulting in significantly improved desolvation compared to conventional arrangements. Furthermore, the nodes of the acoustic standing waves can be adjusted in order to optimise the subsequent transmission of analyte sample into and through the sampling orifice of the mass spectrometer thereby improving sensitivity.

It is apparent, therefore, that the present invention is particularly advantageous.

The droplets may predominantly comprise charged droplets. Alternatively, the droplets may predominantly comprise uncharged or neutral droplets.

The ion source preferably comprises an ultrasonic transmitter or sonotrode and a reflector. Alternatively, the ion source may comprise two ultrasonic transmitters or sonotrodes.

According to the preferred embodiment the ultrasonic transducer is arranged and adapted to emit ultrasonic waves having a frequency in the range: (i) 20-30 kHz; (ii) 30-40 kHz; (iii) 40-50 kHz; (iv) 50-60 kHz; (v) 60-70 kHz; (vi) 70-80 kHz; (vii) 80-90 kHz; (viii) 90-100 kHz; and (ix) >100 kHz.

The one or more ultrasonic transmitters are preferably positioned so that the one or more acoustic standing waves interact with the stream of droplets.

The one or more acoustic standing waves are preferably arranged and adapted to induce internal mixing of the stream of droplets.

The one or more acoustic standing waves may be arranged and adapted to move or translate the stream of droplets.

The one or more acoustic standing waves are preferably arranged and adapted to focus or defocus the stream of droplets.

The one or more acoustic standing waves are preferably arranged and adapted to further nebulise the stream of droplets.

The one or more acoustic standing waves are preferably arranged so as to result in a reduction of the average size of droplets in the stream of droplets.

In a mode of operation the one or more acoustic standing waves are preferably arranged so as to trap at least some droplets for a period of time.

The ion source preferably further comprises a device arranged and adapted to introduce or mix a reagent and/or reagent ions with the droplets.

The reagent and/or reagent ions preferably react or interact with the droplets.

The reagent and/or reagent ions preferably react or interact via Electron Transfer Dissociation, Electron Capture Dissociation, ozonolysis, Hydrogen-Deuterium exchange ("HDx"), charge reduction, photo dissociation or thermal dissociation.

The ion source preferably further comprises a control system arranged and adapted to control the residence time or interaction time between droplets and a reagent and/or reagent ions.

The ion source is preferably maintained in use at Atmospheric pressure, at a pressure greater than atmospheric pressure or at sub-atmospheric pressure.

The one or more ultrasonic transmitters are preferably arranged and adapted to create one or more gas phase acoustic standing waves.

The ionisation device preferably comprises an Atmospheric Pressure Ionisation ("API") ionisation device.

The Atmospheric Pressure Ionisation ionisation device preferably comprises an Electrospray ion source, an Atmospheric Pressure Chemical Ionisation ("APCI") ion source, an Impactor ion source wherein a sample is ionised upon impacting a target, a Laser ion source, an ultra-violet ("UV") photoionisation device or an infra-red ("IR") photoionisation device The ion source preferably further comprises either a Field Induced Droplet Ionisation ("FIDI") ionisation device, a Glow Discharge lamp ionisation device, a laser metastable ionisation device, a Direct Analysis in Real Time ("DART") ionisation device or a secondary ionisation Electrospray ionisation device for ionising droplets held in and/or emerging from the one or more acoustic standing waves.

The ion source preferably further comprises one or more grid electrodes for applying an electric field to droplets held in the one or more acoustic standing waves.

The one or more grid electrodes are preferably at least partially acoustically transparent at a frequency at which the one or more ultrasonic transmitters emit ultrasonic waves.

According to another aspect of the present invention there is provided a mass spectrometer comprising an ion source as described above.

The mass spectrometer preferably comprises an ion inlet. The ion inlet preferably leads from a preferably substantially atmospheric pressure region to a preferably substantially sub-atmospheric pressure region. Analyte molecules and/or ions are preferably arranged to emerge from the one or more acoustic standing waves adjacent the ion inlet so that the analyte molecules and/or ions enter the mass spectrometer via the ion inlet.

The mass spectrometer preferably further comprises a gas phase ion mobility spectrometer or separator, wherein the ion mobility spectrometer or separator is arranged and adapted to separate analyte ions temporally according to their ion mobility.

According to another aspect of the present invention there is provided a method of ionising a sample comprising:
emitting a stream of droplets; and
causing the stream of droplets to interact with one or more acoustic standing waves.

According to another aspect of the present invention there is provided a method of mass spectrometry comprising a method of ionising a sample as described above.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; and (xxi) an Impactor ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter; and/or (k) a device or ion gate for pulsing ions; and/or (l) a device for converting a substantially continuous ion beam into a pulsed ion beam.

The mass spectrometer may further comprise either:

(i) a C-trap and an orbitrap (RTM) mass analyser comprising an outer barrel-like electrode and a coaxial inner spindle-like electrode, wherein in a first mode of operation ions are transmitted to the C-trap and are then injected into the orbitrap (RTM) mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the orbitrap (RTM) mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

BRIEF DESCRIPTION OF THE DRAWINGS

Various embodiments of the present invention will now be described, by way of example only, and with reference to the accompanying drawings in which:

FIG. 1 shows a preferred embodiment of the present invention wherein a stream of droplets is emitted from a liquid source such as an Electrospray ion source and interacts with an acoustic standing wave generated by two sonotrodes or one sonotrode and a reflector.

DETAILED DESCRIPTION OF PREFERRED EMBODIMENTS

A preferred embodiment of the present invention will now be described.

FIG. 1 shows a preferred embodiment of the present invention wherein a stream of droplets is emitted from a liquid source such as an Electrospray ion source and interacts with an acoustic standing wave generated by two sonotrodes or one sonotrode and a reflector.

According to an embodiment one or more standing-wave acoustic fields are introduced into a mass spectrometer (MS) source which has several benefits when an analyte is introduced in a stream of liquid or liquid droplets by e.g. Electrospray.

One of the limitations of known liquid interface MS sources is a loss of analyte due to incomplete desolvation of large droplets. Advantageously, according to the preferred embodiment large droplets can be broken up by acoustic fields. The resulting droplets can be sampled more efficiently into a first vacuum stage of a mass spectrometer and they will also evaporate faster thereby improving the sensitivity of the device.

According to an embodiment of the present invention some additional control of the position of droplets is possible via acoustic lensing within the source region. For example, optimisation of the position of acoustic nodes relative to the sampling orifice enables the transmission into the first vacuum stage to be improved. This improves the sensitivity of the mass spectrometer.

It is known that competition among analytes for the surface layer of droplets can have a significant effect on observed Electrospray MS response (Enke, C., Anal. Chem., 69 (23), 4885-4893, (1997)). Internal mixing induced in the droplets by the acoustic field will advantageously reduce suppression of the signal for species with relatively low surface affinity.

Further enhancement of the atomisation process may be achieved by operating the device above or below atmospheric pressure. According to an embodiment characteristics of the standing acoustic waves such as intensity, node position and frequency of the ultrasound field can also be adjusted. This may be performed either manually or automatically in response to changes in temperature, pressure, flow conditions etc. Feedback from the observed MS signal may be used to control this adjustment.

One or more partially acoustically transparent grids may be positioned close to the region where the acoustic standing waves are generated. The grids may be utilised in order that an electric field for ionisation of the droplets can be applied and sustained without electrical breakdown occurring. The technique can be used to manipulate fields of electrically neutral droplets or charged droplets. Ionisation may occur prior to, inside or following the acoustically active regions.

An additional force may be applied to the droplets to increase the residence time of the droplets in the acoustic field even to the extent of trapping the droplets. Additionally, an electric field may be used to generate ion plumes from the droplets.

Increasing the residence time of droplets has additional benefits when reactions are performed in the MS source region. For example, chemical and physical reactions such as ozonolysis, hydrogen-deuterium exchange, atmospheric pressure ETD/ECD, charge reduction, photo-dissociation and thermal dissociation can be performed.

Reagents which are incompatible with a conventional analyte delivery system (e.g. Electrospray) may advantageously be introduced into the source region of the preferred embodiment. The reaction time with the analyte may be controlled and mixing improved through interaction with the acoustic field.

A yet further advantage of the present invention is that preferential sampling of small droplets or ions by positional manipulation of larger droplets reduces contamination of ion-optical surfaces and sampling orifices, thereby increasing time between cleaning and/or reducing background signals/noise.

Although the present invention has been described with reference to preferred embodiments, it will be understood by those skilled in the art that various changes in form and detail may be made without departing from the scope of the invention as set forth in the accompanying claims.

The invention claimed is:

1. Apparatus for a mass spectrometer comprising:

a device arranged and adapted to emit a stream of droplets;

one or more ultrasonic transmitters or sonotrodes arranged and adapted to create one or more acoustic standing waves downstream of said device;

wherein said one or more acoustic standing waves are arranged and adapted:

to induce internal mixing of said stream of droplets;

to further nebulise said stream of droplets; and to result in a reduction of an average size of droplets in said stream of droplets.

2. Apparatus as claimed in claim 1, wherein said droplets predominantly comprise charged droplets.

3. Apparatus as claimed in claim 1, wherein said droplets predominantly comprise uncharged or neutral droplets.

4. Apparatus as claimed in claim 1, wherein said device comprises an Atmospheric Pressure Ionisation ("API") ionisation device.

5. Apparatus as claimed in claim 1, wherein said one or more ultrasonic transmitters or sonotrodes comprises an ultrasonic transmitter or sonotrode and a reflector.

6. Apparatus as claimed in claim 1, wherein one or more ultrasonic transmitters or sonotrodes comprises two ultrasonic transmitters or sonotrodes.

7. Apparatus as claimed in claim 1, wherein said one or more ultrasonic transmitters are arranged and adapted to emit ultrasonic waves having a frequency in the range: (i) 20-30 kHz; (ii) 30-40 kHz; (iii) 40-50 kHz; (iv) 50-60 kHz; (v) 60-70 kHz; (vi) 70-80 kHz; (vii) 80-90 kHz; (viii) 90-100 kHz; and (ix) >100 kHz.

8. Apparatus as claimed in claim 1, wherein said one or more ultrasonic transmitters are positioned so that said one or more acoustic standing waves interact with said stream of droplets.

9. Apparatus as claimed in claim 1, wherein said one or more acoustic standing waves are arranged and adapted to move or translate said stream of droplets.

10. Apparatus as claimed in claim 1, wherein in a mode of operation said one or more acoustic standing waves are arranged so as to trap said droplets for a period of time.

11. Apparatus as claimed in claim 1, further comprising a device arranged and adapted to introduce or mix a reagent or reagent ions with said droplets.

12. Apparatus as claimed in claim 11, wherein said reagent or reagent ions react or interact with said droplets.

13. Apparatus as claimed in claim 11, wherein said reagent or reagent ions react or interact via Electron Transfer Dissociation, Electron Capture Dissociation, ozonolysis, Hydrogen-Deuterium exchange ("HDx"), charge reduction, photo dissociation or thermal dissociation.

14. Apparatus as claimed in claim 1, further comprising a control system arranged and adapted to control a residence time or interaction time between droplets and a reagent or reagent ions.

15. Apparatus as claimed in claim 1, wherein said one or more ultrasonic transmitters are arranged and adapted to create one or more gas phase acoustic standing waves.

16. Apparatus as claimed in claim 1, further comprising one or more grid electrodes for applying an electric field to droplets held in said one or more acoustic standing waves.

17. Apparatus as claimed in claim 16, wherein said one or more grid electrodes are at least partially acoustically transparent at a frequency at which said one or more ultrasonic transmitters emit ultrasonic waves.

18. A mass spectrometer comprising a device arranged and adapted to emit a stream of droplets;

one or more ultrasonic transmitters or sonotrodes arranged and adapted to create one or more acoustic standing waves downstream of said device;

wherein said one or more acoustic standing waves are arranged and adapted:

to induce internal mixing of said stream of droplets;

to further nebulise said stream of droplets; and to result in a reduction of an average size of droplets in said stream of droplets.

19. A mass spectrometer as claimed in claim 18, wherein said mass spectrometer comprises an inlet.

20. A mass spectrometer as claimed in claim 19, wherein said inlet leads from a substantially atmospheric pressure region to a substantially sub-atmospheric pressure region.

21. A mass spectrometer as claimed in claim 20, wherein analyte molecules or ions are arranged to emerge from said one or more acoustic standing waves adjacent said inlet so that said analyte molecules or ions enter said mass spectrometer via said inlet.

22. A mass spectrometer as claimed in claim 21, further comprising a gas phase ion mobility spectrometer or separator, wherein said ion mobility spectrometer or separator is arranged and adapted to separate analyte ions temporally according to their ion mobility.

23. A method of mass spectrometry comprising:

emitting a stream of droplets; and causing said stream of droplets to interact with one or more acoustic standing waves;

whereby said one or more acoustic standing waves are arranged and adapted:

to induce internal mixing of said stream of droplets;

to further nebulise said stream of droplets; and to result in a reduction of the average size of droplets in said stream of droplets.

* * * * *